United States Patent
Sawacha et al.

(10) Patent No.: US 11,540,768 B2
(45) Date of Patent: Jan. 3, 2023

(54) METHOD AND APPARATUS FOR DETECTING BIOMECHANICAL AND FUNCTIONAL PARAMETERS OF THE KNEE

(71) Applicant: UNIVERSITA' DEGLI STUDI DI PADOVA, Padua (IT)

(72) Inventors: Zimi Sawacha, Padua (IT); Davide Pavan, Padua (IT); Federica Cibin, Monastier (IT); Giorgio Sbrocco, Rubano (IT); Annamaria Guiotto, Campodarsego (IT); Claudio Cobelli, Padua (IT); Fabiola Spolaor, Mirano (IT)

(73) Assignee: UNIVERSITA DEGLI STUDI DI PADOVA, Padua (IT)

( * ) Notice: Subject to any disclaimer, the term of this patent is extended or adjusted under 35 U.S.C. 154(b) by 546 days.

(21) Appl. No.: 16/608,866

(22) PCT Filed: Apr. 26, 2018

(86) PCT No.: PCT/IB2018/052904
§ 371 (c)(1),
(2) Date: Oct. 28, 2019

(87) PCT Pub. No.: WO2018/198066
PCT Pub. Date: Nov. 1, 2018

(65) Prior Publication Data
US 2020/0275881 A1    Sep. 3, 2020

(30) Foreign Application Priority Data
Apr. 28, 2017  (IT) .................... 102017000046512

(51) Int. Cl.
*A61B 5/00* (2006.01)
*A61B 5/103* (2006.01)
*A61B 5/11* (2006.01)

(52) U.S. Cl.
CPC .......... *A61B 5/4585* (2013.01); *A61B 5/0077* (2013.01); *A61B 5/1036* (2013.01);
(Continued)

(58) Field of Classification Search
CPC ... A61B 5/4585; A61B 5/0077; A61B 5/1036; A61B 5/1114; A61B 5/1122;
(Continued)

(56) References Cited

U.S. PATENT DOCUMENTS 9,763,604 B1* 9/2017 Berme ............... A63B 69/0053
2010/0094174 A1* 4/2010 Choi .................... A61B 5/1127
600/587

(Continued)

FOREIGN PATENT DOCUMENTS

WO    2015103359 A1    7/2015

OTHER PUBLICATIONS

Silvia Del Din et al: "Impaired gait in ankylosing spondylitis", Medical & Biological Engineering & Computing, Springer, Berlin, DE, vol. 49, No. 7, Jan. 13, 2011.

(Continued)

Primary Examiner — Patrick Fernandes
(74) Attorney, Agent, or Firm — Mark M. Friedman

(57) ABSTRACT

Method for detecting biomechanical and functional parameters of the knee in a situation of performance stress, which comprises: a step for the set up of video recording means (1); a step for the set up of multiple optical markers (4) at specific landmark anatomic points (PA) of the foot and of the knee of a person; a step for the set up, at the plantar surface of the foot, of baropodometric means (5); a step for the acquisition, by means of the video recording means (1), of images of at least one reference action, and a step for the detection, by means of the baropodometric means (5), of baropodometric parameters; a step for calculating, from the baropodometric (Continued)

parameters, the coordinates of the center of pressure (COP) of the foot and of the constraining reaction force (FV) acting on the foot; a step for calculating a force arm (BF) given by the distance between the center of pressure (COP) and a reference point (PR) of the knee; a step for calculating a biomechanical parameter indicative of the valgus moment, derived from the vector product (PV) of the force arm (BF) and the constraining reaction force (FV).

11 Claims, 3 Drawing Sheets

(52) U.S. Cl.
CPC .......... *A61B 5/1114* (2013.01); *A61B 5/1122* (2013.01); *A61B 5/1127* (2013.01); *A61B 5/6807* (2013.01); *A61B 2503/10* (2013.01); *A61B 2560/0223* (2013.01); *A61B 2562/046* (2013.01)

(58) Field of Classification Search
CPC . A61B 5/1127; A61B 5/6807; A61B 2503/10; A61B 2560/0223; A61B 2562/046
See application file for complete search history.

(56) References Cited

U.S. PATENT DOCUMENTS

| | | | |
|---|---|---|---|
| 2014/0148931 A1* | 5/2014 | Watanabe | A61B 5/1121 700/92 |
| 2017/0027803 A1* | 2/2017 | Agrawal | A61B 5/1122 |

OTHER PUBLICATIONS

Alice Mantoan et al: "M0toNMS: A MATLAB toolbox to process motion data for neuromusculoskeletal modeling and simulation", Source Code for Biology and Medicine, Dec. 16, 2015.

Zimi Sawacha et al: "Biomechanical assessment of balance and posture in subjects with ankylosing spondylitis", Journal of Neuroengineering and Rehabilitation, Biomed Central, London, GB, vol. 9, No. 1, Aug. 29, 2012.

Grood, Edward & Suntay W.J. (1983). "A Joint Coordinate System for the Clinical Description of Three-Dimensional Motions: Application to the Knee". Journal of biomechanical engineering.

Zimi Sawacha, Giuseppe Cristoferi, Gabriella Guarneri, Stefano Corazza, Giulia Dona, Paolo Denti, Andrea Fachinetti, Angelo Avogaro, and Claudio Cobelli,"Characterized multisegment foot kinematics during gait in diabetic foot patients", Journal of NeuroEngineering and Rehabilitation, Oct. 23, 2019.

Susan M. Sigward, Christopher M. Powers, "Loading characteristics of females exhibiting excessive valgus moments during cutting", Apr. 3, 2007.

Fabricio A. Magalhaes, Zimi Sawacha, Rocco Di Michele, Matteo Cortesi, Giorgio Gatta and Silvia Fantozzi, "effectiveness of an Automatic Tracking Software in Underwater Motion Analysis", Dec. 1, 2013.

Scott G. McLean, Xuemei Huang, Anne Su, Antonie J. Van Den Bogret, "Sagittal plane biomechanics cannot injure the ACL during sidestep cutting".

Colin W Fuller, John H M Brooks, Rebecca J Cancea, John Hall Simon P T Kemp, "Contact events in rugby union and their propensity to cause injury", May 18, 2007.

Gregory D. Myer, Kevin R. Ford, Jane Khoury, Paul Succop, and Timothy E. Hewett, Development and Validation of a Clinic-Based Prediction Tool to Identify Female Athletes at High Risk for Anterior Cruciate Ligament Injury, Oct. 2010.

Darin A. Padua, Michelle C. Boling, Lindsay J. Distefano, James A. Onate, Anthony I. Beutler, and Stephen W. Marshall, Reliability of the Landing Error Scoring System-Real Time, a Clinical Assessment Tool of Jump-Landing Biomechanics.

Keith A. Stokes, Simon P. Roberts, Grant Trewartha, Mike England, "Collapsed scrums and collision tackles: what is the risk?".

Choongsoo S. Shin, Ajit M. Chaudhari, and Thomas P. Andriacchi, "Valgus Plus Internal Rotation Moments Increase Anterior Cruciate Ligament Strain More Than Either Alone", vol. 43, No. 8, 2011.

* cited by examiner

METHOD AND APPARATUS FOR DETECTING BIOMECHANICAL AND FUNCTIONAL PARAMETERS OF THE KNEE

FIELD OF APPLICATION

The present invention refers to a method and to an apparatus for detecting biomechanical and functional parameters of the knee, in particular in a situation of performance stress, in order to estimate the risk of injury to the anterior cruciate ligament.

The present method and apparatus are inserted in the field of design and production of systems for evaluating the risk of injury to joints, and in particular to the knee.

Advantageously the present method and apparatus are intended to be employed, in particular in sports, for detecting biomechanical parameters, such as in particular the valgus moment of the knee, by means of which it is possible to obtain information and estimates relative to the possibility of onset of an injury to the anterior cruciate ligament of a person and, in particular, of an athlete while practicing a sport activity.

State of the Art

As is known, in sports, injuries to joints occur frequently, in particular to the anterior cruciate ligament of the knee. These injuries oblige athletes to interrupt their sport activity for long periods, and such athletes are subjected to surgical operations and numerous rehabilitation sessions for the healing thereof.

Much scientific research has been undertaken aimed to recognize the game situations in the various sports activities most prone to injury of the anterior cruciate ligament and to study the recurring causes and dynamics of such injury in order to retrieve information useful for the prevention thereof.

In particular, it has emerged that injuries to the anterior cruciate ligament frequently occur in situations of non-contact during unilateral landing or lateral cutting movements (such as change in direction in soccer, rugby, basketball, volleyball; landing after blocking, spiking or serving the volleyball; landing after shooting the basketball; tackling in rugby).

For example, in the case of rugby, the research conducted on the risk of injury to the anterior cruciate ligament has indicated that the most dangerous game situations are scrum and tackling. More in detail, the research conduct on the risk of lesions to the cruciate ligament has shown that, even if the scrum is the most probable time that athletes report lesions, tackling is the event during which the most injuries occur, due to the contact with the adversary and the high number of executions of such activity during matches (Fuller et al., 2007, "Contact events in rugby union and their propensity to cause injury", British Journal of Sports Medicine 41, 862-867; Roberts et al., 2015, "Collapsed scrums and collision tackles: what is the injury risk?" British Journal of Sports Medicine 49, 536-540).

The mechanisms of injury to the anterior cruciate ligament have been studied for some time in the field of biomechanics and movement analysis, together with studies for planning prevention measures.

In particular, predictive risk variables have been identified which have brought the attention towards the forces acting in the joint along the front and transverse planes (Mc Lean et al., 2004, "Sagittal plane biomechanics cannot injure the ACL during sidestep cutting" Clinical Biomechanics, 828-838). More in detail, the variables deemed effective in preventing the injury to the anterior cruciate ligament have proven to be the valgus moment and excessive bending, since they would lead to an intra-rotation of the tibial plate, with consequent tension on the anterior cruciate ligament (Shin et al., 2011, "Valgus plus internal rotation moments increase anterior cruciate ligament strain more than either alone" Med Sci Sports Exerc. 2011 August; 43(8):1484-91).

Methods are known for evaluating the risk of injury to the anterior cruciate ligament, which require executing movement tests in analysis laboratories and provide for the kinetic and kinematic evaluation of the knee according to different protocols, such as the drop jump test (Padua et al., 2011, "Reliability of the landing error scoring system-real time, a clinical assessment tool of jump-landing biomechanics", Journal of Sport Rehabilitation 20, 145-156).

Methods are also known for evaluating the risk of injury to the ligaments which provide for executing an indirect estimate of the valgus moment, for example by using parameters correlated with such moment such as articular trunk, knee, angle and hip angles (Padua et al., 2011, "Reliability of the landing error scoring system-real time, a clinical assessment tool of jump-landing biomechanics", Journal of Sport Rehabilitation 20, 145-156), or incorrect alignments of the knee with respect to the axis of the tibia, anthropometric measurements provided with force measurements carried out by means of isokinetic machines (Myer et al., 2010, "Development and validation of a clinic-based prediction tool to identify female athletes at high risk for anterior cruciate ligament injury", The American Journal of Sports Medicine 38, 2025-2033).

The latter methods require the use of video recording systems (multi-camera or single-camera) and the use of isokinetic machines.

One example of a method that employs video recording systems for recording human movements, for the purpose of providing quantitative parameters on the risk of injury, is described in the patent application WO 2015/103359.

These methods of known type have in practice demonstrated that they do not lack drawbacks.

A first drawback is due to the fact that the aforesaid methods must be carried out in movement analysis laboratories, requiring the use of specific instruments and isokinetic machines, therefore involving structures that are often not easily accessible to sports companies/teams due to costs and complexity.

A further drawback is due to the fact that the abovementioned methods of known type involve long execution times, in particular requiring athletes to undertake the tests outside of sports facilities and outside normal training sessions.

A further drawback is due to the fact that the abovementioned methods of known type are only actuatable by means of the execution of motor movements according to specific protocols and, therefore, are not directly indicative of the risk of injury in the specific athletic movements of the different sports disciplines (e.g. change of direction, landing after jumping/spiking, landing after shooting the basketball, tackling in rugby).

In addition, the methods which provide for the indirect calculation of the valgus moment require executing a high number of measurements, with consequent long test execution times.

Presentation of the Invention

The main object of the present invention is therefore to overcome the drawbacks manifested by the solutions of known type, by providing a method and an apparatus for detecting biomechanical and functional parameters of the knee which can be actuated in a simple and inexpensive manner, in particular during normal training sessions and without requiring the use of movement analysis laboratories.

Another object of the present invention is to provide a method and an apparatus for detecting biomechanical and functional parameters of the knee which allow obtaining information regarding the risk of injury to the anterior cruciate ligament indicative for specific sports disciplines, in particular being employable with specific athletic movements of the sports disciplines.

BRIEF DESCRIPTION OF THE DRAWINGS

The technical characteristics of the invention, according to the aforesaid objects, can be clearly seen in the contents of the below-reported claims and the advantages thereof will be more evident from the following detailed description, made with reference to the enclosed drawings, which represent a merely exemplifying and non-limiting embodiment of the invention, in which:

DETAILED DESCRIPTION OF A PREFERRED EMBODIMENT

The present method and apparatus are inserted in the field of design and production of systems for evaluating the risk of injury to joints, and in particular to the knee.

Advantageously the present method and apparatus are intended to be employed, in particular in sports, for detecting biomechanical parameters indicative of the valgus moment of the knee, by means of which it is possible to obtain information and estimates relative to the possibility of onset of an injury to the anterior cruciate ligament of the knee of a subject, in particular, of an athlete during the practice of a sport activity.

The present method comprises a step for the set up of video recording means 1 adapted to frame a scene, in which one or more people complete at least one specific reference action, as described in detail hereinbelow.

Figure 1:
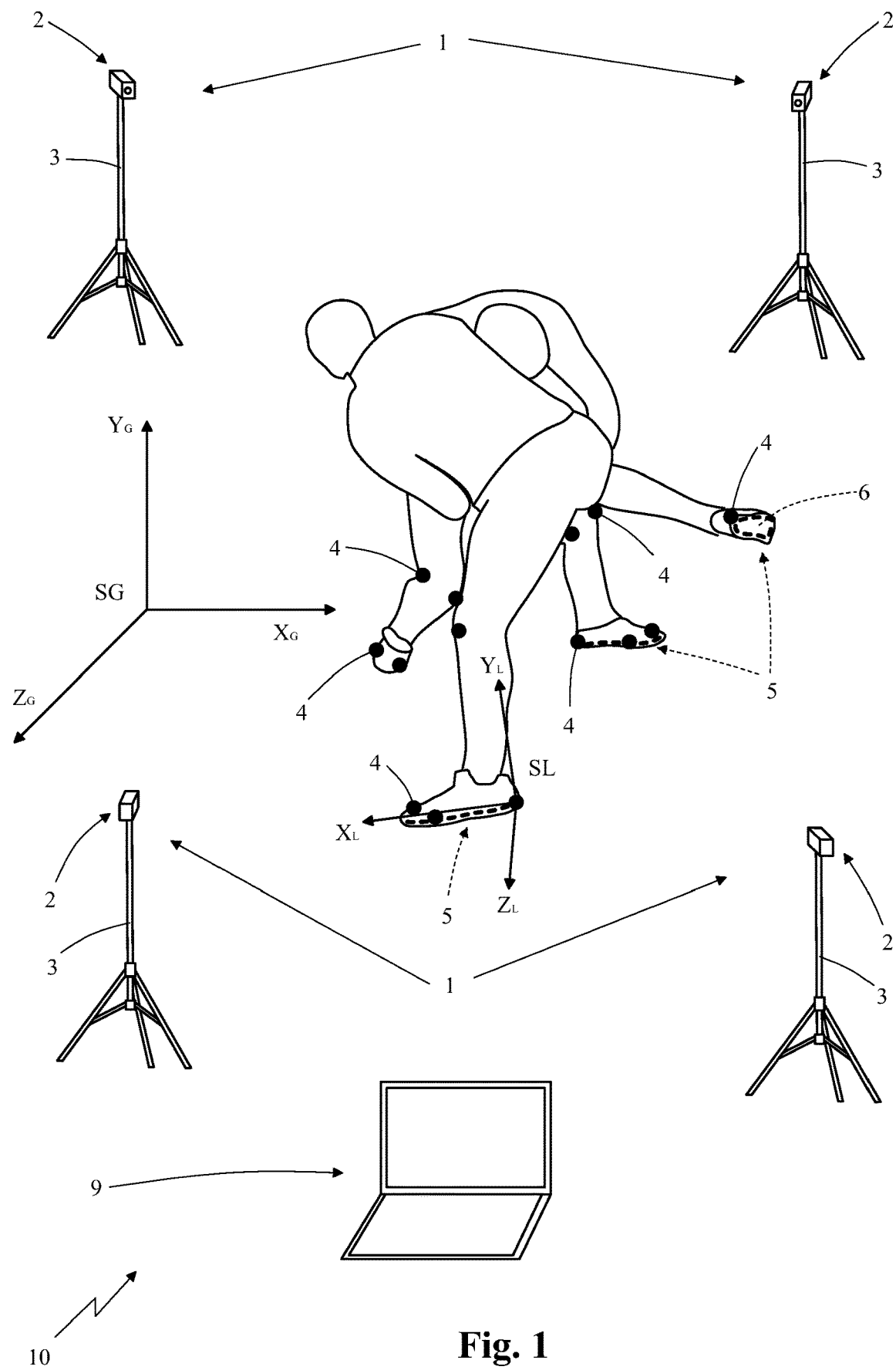
FIG. 1 shows the apparatus, object of the present invention, during a step for image acquisition of the present method.

Advantageously, in accordance with the example of FIG. 1, the video recording means 1 comprise at least two cameras 2, e.g. four, configured to acquire, for example, thirty images per second.

Preferably, in the aforesaid step for the set up of the video recording means 1, the cameras 2 are arranged on corresponding stands 3, in particular at about two meters from the ground, in a manner such to frame the entire scene and ensure the visibility of the reference action.

The present method comprises a step for defining, in the scene framed by the video recording means 1, a global reference system SG integral with the video recording means 1 themselves, and in particular integral with the cameras 2.

Preferably, the global reference system SG is a three-dimensional reference system, in particular Cartesian, with axes $X_G$, $Y_G$, $Z_G$.

Advantageously, the step for defining the global reference system SG is obtained by means of a process for calibrating the video recording means 1, and in particular the cameras 2.

For example, the calibration process (and in particular the calculation of the extrinsic and intrinsic calibration parameters of the cameras 2) is obtained by employing a reference table (checkboard) in the scene and by employing a software of known type for calibrating the cameras, such as "Camera Calibration Toolbox for Matlab®" by Jean-Yves Bouguet (http://www.vision.caltech.edu/bouguetj/calib_doc/,2010).

The present method comprises a step for the set up of multiple optical markers 4 at specific anatomical points PA of at least one foot and of the corresponding knee of the person who will execute the reference action to be recorded.

Advantageously, the aforesaid anatomical points PA are selected from among a specific group of landmark points comprising the calcaneus $PA_{CA}$, the first metatarsal head $PA_{IMH}$, the fifth metatarsal head $PA_{VMH}$, the lateral epicondyle of the femur $PA_{LE}$ and the medial epicondyle of the femur $PA_{ME}$.

The anatomical points PA identify a local reference system SL integral with the foot in particular by means of the landmark points of the calcaneus $PA_{CA}$, of the first metatarsal head $PA_{IMH}$ and of the fifth metatarsal head $PA_{VMH}$, for example as defined in the scientific publication "Characterizing multisegment foot kinematics during gait in diabetic foot patients" by Sawacha and al. Journal of NeuroEngineering and Rehabilitation 2009, 6:37.

Preferably, the local reference system SL is a three-dimensional reference system, in particular Cartesion, with axes $X_L$, $Y_L$, $Z_L$.

Figure 3:
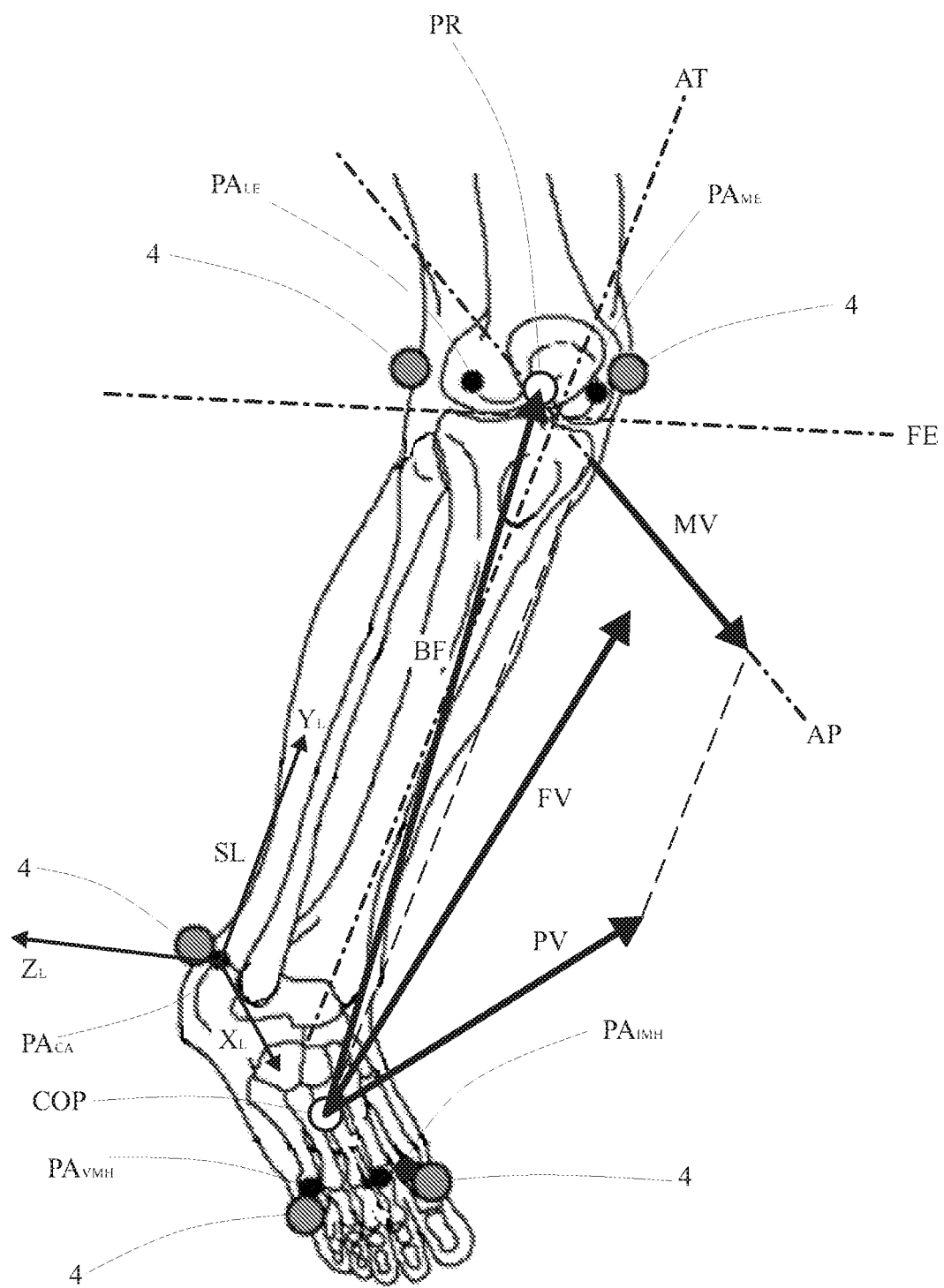
FIG. 3 shows optical markers of the present apparatus applied to the foot and to the leg of a person with local reference system of the foot indicated.

In addition, in accordance with the example of FIG. 3, the anatomical points PA identify a reference point of the knee PR, for example given by the medial point between the landmark point of the lateral epicondyle of the femur $PA_{LE}$ and the medial epicondyle of the femur $PA_{ME}$, or, in accordance with a different implementation, by the landmark point of the lateral epicondyle of the femur $PA_{LE}$ if both the points $PA_{LE}$ and $PA_{ME}$ are not visible to the cameras 2.

In particular, the optical markers 4 employed for identifying the anatomical points PA are of passive type and for example comprise bichromatic labels or labels made of reflector material. A particular example of optical markers 4 is described in "Effectiveness of an automatic tracking software in underwater motion analysis" by Magalhaes, Sawacha, Di Michele, Gatta, Fantozzi, Journal of Sports Science and Medicine, 2013, 12 (4), pp. 660-667.

According to the invention, the present method comprises a step for the set up, at the plantar surface of at least one foot of the person, of baropodometric means 5 integral with the local reference system SL of the foot itself.

Preferably, the baropodometric means 5 are arranged at both feet of the person and, if the reference action is completed by multiple people, the baropodometric means 5 are arranged at both feet of such people.

Advantageously, the baropodometric means 5 comprise at least one pressure insole 6 which, in the aforesaid step for the set up of the baropodometric means 5, is inserted in a footwear worn by the corresponding foot in order to be subjected to the action of the plantar surface of such foot during the reference action carried out by the corresponding person.

Figure 2:
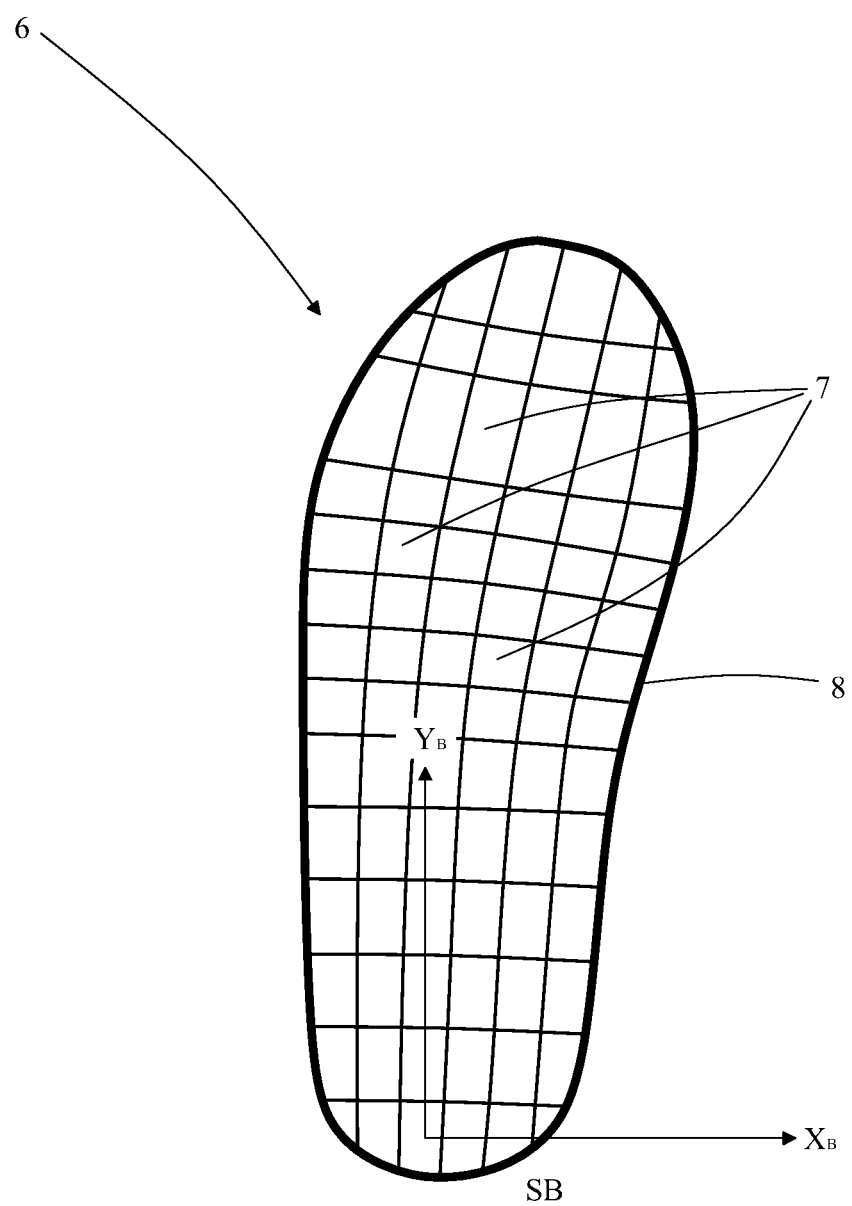
FIG. 2 shows, in a schematized manner, a detail of the apparatus, object of the present invention, relative to a pressure insole of baropodometric means.

Preferably, with reference to the example of FIG. 2, each pressure insole 6 is provided with an array of sensors 7, in particular pressure sensors, for example of capacitive or resistive type.

Suitably, the pressure insole comprises a flexible plantar support 8 shaped to substantially cover the entire plantar surface of the foot and on which the sensors 7 are distributed so to be able to monitor the pressures imparted in the various regions of the foot itself.

In particular, the array of sensors 7 comprises several dozen sensors, e.g. between about 80 and about 100 sensors, as a function of the size of the pressure insole 6.

For example, pressure insoles produced by Novel GmbH with sensors of capacitive type can be employed.

The sensors 7 of each pressure insole 6 are positioned in a baropodometric reference system SB of the pressure insole 6 integral with the local reference system SL of the foot to which the pressure insole 6 itself is applied.

In particular, the baropodometric reference system SB of the pressure insole 6 is a two-dimensional reference system, in particular Cartesian, with axes $X_B$, $Y_B$, substantially parallel to the plantar support 8 of the pressure insole 6.

The baropodometric reference system SB of the pressure insole 6 is related to the local reference system SL of the corresponding foot by means of a specific transformation relation of the coordinates, for example identified by associating a specific sensor 7 of the pressure insole 6 (arranged in specific coordinates of the baropodometric reference system SB) with the origin of the local reference system SL (for example constituted by the landmark point of the calcaneus $PA_{CA}$).

The present method comprises a step for the acquisition, by means of the aforesaid video recording means 1, of images of at least one reference action executed in the scene by the person provided with the optical markers 4 and the baropodometric means 5.

In such reference action, the person executes at least one support movement of the foot on a support plane of the scene, such as the ground of a sports field where the reference action is executed.

Advantageously, with reference to the example of FIG. 1, the reference action completed in the step for image acquisition comprises a tackling movement of the game of rugby, in particular executed by following the guidelines of the South Africa Rugby Union.

Of course, the reference action completed in the step for image acquisition will be determined as a function of the particular situations where the present method is applied and in particular as a function of the sports discipline practiced by the person subjected to the method. For example, the reference action completed in the step for image acquisition can comprise jumping for spiking the volleyball, jumping for shooting the basketball, etc.

The method according to the invention also comprises a step for the detection, by means of the aforesaid baropodometric means 5, of baropodometric parameters indicative of dynamic interactions exchanged between the foot and the support plane of the scene during the step for image acquisition.

In particular, the aforesaid detection parameters comprise measurements of the plantar pressures exerted by the foot within the shoe, in particular detected by means of the sensors 7 of the pressure insole 6.

Advantageously, the present method comprises a step for the time synchronization between the cameras 2 and the baropodometric means 5, in a manner such to temporally correlate the images acquired by the cameras 2 in each sampling instant with the baropodometric parameters acquired by the baropodometric means 5 in the corresponding sampling instants.

In particular, the synchronization step can be actuated during the step for the image acquisition or afterwards, for example—in a manner per se known to the man skilled in the art—regarding the recognition of specific time instants, such as the instant of the first separation of the foot from the ground.

Advantageously, the images acquired by the video recording means 1 and the baropodometric parameters detected by the baropodometric means 5 are transferred to an electronic processing unit 9 provided with processor, and for example comprising a computer.

For such purpose, in particular, the cameras 2 and the pressure insoles 6, during the steps of image acquisition and detection, are connected to the processing unit 9 via cable (e.g. by means of an optical fiber/USB cable) or in wireless mode (e.g. by means of Bluetooth technology or Wi-Fi). Otherwise, the cameras 2 and the pressure insoles 6 are provided with respective local memories (such as flash internal memories) in which the data relative to the images and the baropodometric parameters is saved, in a manner such to be able to afterwards transfer such data to the processing unit 9.

Preferably, the processing unit 9 is provided with one or more implementation programs adapted to process the data relative to the images and to the baropodometric parameters acquired for calculating the valgus moment of the knee, in accordance with operating steps described in detail hereinbelow.

More in detail, the present method comprises a step for calculating the 3D trajectories of the optical markers 4 in the global reference system SG during the reference action recorded by the video recording means 1 in order to identify the coordinates of the corresponding anatomical points PA in the global reference system SG itself.

In this manner, in particular, at each sampling instant, the aforesaid step for calculating the trajectories determines the position of the axes $X_L$, $Y_L$, $Z_L$ of the local reference system SL of the foot in the global reference system SG, in order to determine the relative transformation relations between local reference system SL and global reference system SG and, therefore, the transformation relations between the coordinates of the baropodometric reference system SB of the pressure insole 6 associated with the foot and the coordinates of the global reference system SG.

In addition, the aforesaid step for calculating the trajectories determines the coordinates of the reference point PR of the knee in the global reference system SG, which will be employed for calculating a force arm as described in detail hereinbelow.

In particular, the step for calculating the trajectories of the optical markers 4 is implemented, in a manner per se known to the man skilled in the art, by means of a video tracking software installed in the processing unit 9.

The method also comprises a step for calculating, from the baropodometric parameters detected by the baropodometric means 5, the constraining reaction force FV acting on the corresponding foot during the reference action, in particular from the pressure measurements detected by the sensors 7 of the pressure insole 6 related to the support are of the foot at each sampling instant.

In particular, the step for calculating the constraining reaction force FV allows reconstructing the time progression of the constraining reaction force FV on each foot during the image acquisition step, in particular allowing the identification of the peak of such time progression.

The present method also comprises a step for calculating, from the baropodometric parameters detected by the baropodometric means 5, the coordinates of the center of pressure COP of the foot with respect to the local reference system SL during the reference action.

In particular, the center of pressure COP is defined as the projection of the center of gravity of the person over the support area of the foot on the reference plane.

For example, the center of pressure COP is obtained from the pressure measurements of the sensors 7 of the pressure insole 6, for example by means of a weighted average, over space, of the pressures measured also as a function in particular of the weight and height of the person.

In particular, the coordinates of the center of pressure COP vary during the reference action, defining a progression that is obtained in the aforesaid step for calculating the coordinates of the center of pressure COP.

Preferably, the coordinates of the center of pressure COP are calculated in the baropodometric reference system SB of the corresponding pressure insole 6 and, as described in detail hereinbelow, will be transformed into the coordinates of the global reference system SG through the local reference system SL of the foot. Suitably, the steps for calculating the constraining reaction force FV and the coordinates of the center of pressure COP are implemented by means of a calculation software, installed in the processing unit 9, and obtained for example by means of the Novel Pedar X-software produced by Novel GmbH.

According to the invention, the method comprises a step for transforming the coordinates of the center of pressure COP in the global reference system SG.

Advantageously, the coordinates of the center of pressure COP are transformed from the baropodometric reference system SB of the corresponding pressure insole 6, integral with the local system SL of the corresponding foot, to the global reference system SG. In particular, the transformation step is obtained by means of the (fixed) transformation relation between the baropodometric reference system SB and the corresponding local reference system SL, and by means of the transformation relation between such local reference system SL and the global reference system SG derived from the coordinates of the anatomical points PA obtained in the preceding step for calculating the trajectories of the optical markers 4.

In particular, the transformation of the coordinates of the center of pressure COP from the baropodometric reference system SB to the global reference system SG is obtained by means of a roto-translation transformation of such coordinates.

The method then comprises a step for calculating a force arm BF given by the distance between the center of pressure COP and the reference point of the knee PR. In particular, such step for calculating the force arm BF is obtained by means of the coordinates of the center of pressure COP in the global reference system SG (obtained in the aforesaid transformation step) and the coordinates of the reference point of the knee PR in the same global reference system SG (obtained in the aforesaid step for calculating the trajectories of the optical markers 4). The calculation of the force arm BF is made possible by the transformation of the coordinates of the center of pressure COP from the baropodometric reference system SB of the pressure insole 6 to the global reference system SG through the definition of the local reference system SL of the foot.

According to the invention, the present method comprises a step for calculating a biomechanical parameter indicative of the valgus moment acting on the knee during the reference action recorded in the step for image acquisition.

In particular, the aforesaid biomechanical parameter is derived from the vector product PV of the force arm BF and the constraining reaction force FV applied on the center of pressure COP.

Preferably, such vector product PV is given by a three-dimensional vector in the global reference system GB that can be varied during the reference action executed by the person.

Advantageously, in the step for calculating the biomechanical parameter, the latter is calculated by the projection MV of the aforesaid vector product on an anterior-posterior axis AP of the knee, in particular in order to obtain the component of the twisting moment that defines the possible abduction or adduction rotation of the knee.

In particular, with reference to the example of FIG. 3, the aforesaid anterior-posterior axis AP of the knee can be defined as an axis parallel to the long axis of the foot (such long axis of the foot being identified by the optical marker 4 placed at the landmark point of the calcaneus $PA_{CA}$ and by the medial point between the landmark points of the first metatarsal head $PA_{IMH}$ and of the fifth metatarsal head $PA_{VMH}$) translated at the reference point of the knee PR. If, in accordance with a different embodiment, it is desired to maintain the conventional definition of the anterior-posterior axis of the knee, it is possible to apply a further optical marker on the femur at the landmark anatomic point corresponding to the trochanter major and four further optical markers on the hip at the anterior (right and left) iliac spines and at the posterior (right and left) iliac spines. In both embodiments, the anterior-posterior axis of the knee is defined such to be orthogonal to the bending-extension axis FE of the knee, for example as described in the publication "A joint coordinate system for the clinical description of the three dimensional motion: application to the knee" by Grood and Suntay, Journal of Biomechanical Engineering 1983. If three further optical markers are applied at the landmark anatomic points corresponding to the two medial and lateral malleoli and to the head of the fibula, it will be possible to completely replicate the reference system proposed in the aforesaid Grood and Suntay publication and determine an axis of abduction/adduction of the knee orthogonal to the internal and external rotation axis of the tibia defined by means of the vector defined through the medial point between the two optical markers placed at the two malleoli and the optical marker at the head of the fibula.

Advantageously, in the aforesaid step for calculating the biomechanical parameter, the latter is normalized with respect to one or more anthropomorphic parameters of the person, such as in particular body mass and height in order to make such biomechanical parameter comparable with that of other subjects or with reference values.

Preferably, the projection MV of the vector product PV on the anterior-posterior axis AP is normalized with respect to the body mass and height of the corresponding person.

In accordance with a particular embodiment of the present method, the values of the biomechanical parameter are obtained at specific reference instants of the step for the image acquisition, such as the instants where the peak values of the constraining reaction force FV are verified.

Otherwise, the values of the biomechanical parameter are obtained at substantially all the sampling instants.

Advantageously, a step can be implemented for comparing the biomechanical parameter calculated with one or more threshold values known in the literature of the field, such as the threshold value defined in "Loading characteristics of females exhibiting excessive valgus moments during cutting" by Sigward and Powers, 2007 Clinical Biomechanics 22, 827-833.

In particular, a significant risk of injury to the knee can be identified in the presence of values of the biomechanical parameter higher than the aforesaid threshold value.

Also forming the object of the present invention is an apparatus 10 for detecting the valgus moment at the knee, and such apparatus 10, in particular, is employable for automatically executing the above-described method.

The apparatus 10 that is the object of the present invention comprises multiple optical markers 4 intended to be arranged at specific anatomical points PA of the foot and at the corresponding knee of the person, in a manner such to identify a local reference system SL integral with the foot and at least one reference point PR of the knee, in accordance in particular with that described above.

The apparatus 10 also comprises baropodometric means 5 configured for being arranged at the plantar surface of the foot in a manner integral with the local reference system SL of the latter.

Advantageously, the baropodometric means 5 comprise one or more pressure insoles 6 described in detail above.

The baropodometric means 5 are configured for detecting baropodometric parameters indicative of dynamic interactions exchanged between the foot and the support plane of the scene, and in particular for detecting, by means of the sensors 7 of the pressure insoles 6, measurements of the pressures exerted by the foot.

The apparatus also comprises video recording means 1, such as two or more cameras 2, adapted to frame a scene and calibrated with a global reference system SG as defined above.

The video recording means 1 are configured for recording at least one reference action executed in the scene by the person provided with the optical markers 4 and with the baropodometric means 5.

The apparatus 10, object of the present invention, comprises at least one processing unit 9 configured to receive the images from the video recording means 1 and the baropodometric parameters from the baropodometric means 5, in order to process them to obtain values of a biomechanical parameter indicative of the valgus moment of the knee during the reference action.

More in detail, the processing unit 9 is provided with a first calculation module configured to calculate the trajectories of the optical markers 4 in the global reference system SG during the reference action and to identify the coordinates of the anatomical points PA in the global reference system SG, in a manner such to determine the position of the local reference system SL of the foot with respect to the global reference system SG and the coordinates of the reference point PR of the knee in the global reference system SG itself.

In addition, the processing unit 9 is provided with a second calculation module configured to calculate, from the baropodometric parameters, the coordinates of the center of pressure COP of the foot with respect to the local reference system SL.

Advantageously, the second calculation module of the processing unit 9 is configured to calculate the coordinates of the center of pressure COP in the baropodometric reference system SB, as discussed above.

The processing unit 9 is also provided with a third calculation module configured to transform the coordinates of the center of pressure COP in the global reference system SG, and in particular, to transform the coordinates of the center of pressure COP from the baropodometric reference system SB of the pressure insole 6 to the global reference system SG through the local reference system SL, in accordance with that described above.

In addition, the third calculation module is configured to calculate, from the baropodometric parameters, and in particular from the pressure measurements executes by the sensors 7 of the pressure insole 6, the constraining reaction force FV acting on the foot during the reference action.

In addition, the third calculation module is configured to calculate a force arm BF given by the distance between the center of pressure COP and the reference point PR of the knee, by means of the coordinates of the center of pressure COP and of the reference point PR in the global reference system SG.

The third calculation module is configured to calculate a biomechanical parameter indicative of the valgus moment derived from the vector product PV of the force arm BF and the constraining reaction force FV applied on the center of pressure COP.

Advantageously, the third calculation module is arranged to calculate the biomechanical parameter from the projection MV of the aforesaid vector product PV on an anterior-posterior axis AP of the knee, in particular in order to obtain the component of the twisting moment that defines the possible abduction or adduction rotation of the knee.

Advantageously, the third calculation module is arranged for normalizing the biomechanical parameter, and in particular the aforesaid projection MV, with respect to one or more anthropomorphic parameters of the person who completed the reference action, such as in particular the body mass and the height in order to make such biomechanical parameter comparable with those of other subjects or with reference values.

Preferably, the aforesaid calculation modules of the processing unit 9 are implemented by means of one or more softwares installed in a same hardware device of the processing unit 9 itself.

Otherwise, the calculation modules of the processing unit 9 can be obtained by means of separate hardware devices.

The invention thus described therefore attains the preestablished objects.

The invention claimed is:

1. A Method for detecting biomechanical and functional parameters of a knee, said method comprising:
    a step for set up of video recording elements adapted to frame a scene;
    a step for defining, in said scene, a global reference system integral with said video recording elements;
    a step for set up of a plurality of optical markers at defined anatomical points of a foot and of a corresponding knee of a person, and said defined anatomical points identify a local reference system integral with said foot and a reference point of said corresponding knee;
    a step for set up, at a plantar surface of said foot, of baropodometric elements integral with said local reference system;
    a step for acquisition, through said video recording elements, of images of at least one reference action executed in said scene by said person provided with said plurality of optical markers and with said baropodometric elements, and in said at least one reference action said person executes at least one support movement of said foot on a support plane of said scene;
    a step for detection, through said baropodometric elements, of baropodometric parameters indicative of dynamic interactions exchanged between said foot and said support plane during said step for acquisition of images;

a step for calculating trajectories of said plurality of optical markers in said global reference system during said at least one reference action, identifying coordinates of said defined anatomical points in said global reference system;

a step for calculating, from said baropodometric parameters, coordinates of a center of pressure of said foot with respect to said local reference system during said at least one reference action;

a step for transforming the coordinates of said center of pressure in said global reference system;

a step for calculating, from said baropodometric parameters, a constraining reaction force acting on said foot during said at least one reference action;

a step for calculating a force arm given by a distance between said center of pressure and said reference point of said corresponding knee, through the coordinates of said center of pressure and of said reference point in said global reference system;

a step for calculating a biomechanical parameter indicative of a valgus moment, and derived from a vector product of said force arm and said constraining reaction force applied on said center of pressure.

2. The method of claim 1, wherein said baropodometric elements comprise at least one pressure insole which, in said step for set up of said baropodometric elements, is inserted into a footwear worn by said foot to be subjected to said dynamic interactions during said at least one reference action.

3. The method of claim 2, wherein said at least one pressure insole is provided with an array of sensors placed in a baropodometric reference system integral with said local reference system of said foot;

in said step for calculating the coordinates of said center of pressure, the coordinates of said center of pressure being identified in said baropodometric reference system;

in said step for transforming the coordinates of said center of pressure in said global reference system, the coordinates of said center of pressure being transformed from said baropodometric reference system to said global reference system through said local reference system of said foot.

4. The method of claim 1, wherein said defined anatomical points are selected from a group of landmark points comprising: calcaneus, first metatarsal head, fifth metatarsal head, lateral epicondyle of femur, medial epicondyle of femur.

5. The method of claim 1, further comprising a step for time synchronization of said video recording elements with said baropodometric elements.

6. The method of claim 1, wherein, in said step for calculating said biomechanical parameter, said biomechanical parameter is calculated by a projection of said vector product on an anterior-posterior axis of said corresponding knee.

7. The method of claim 1, wherein said video recording elements comprise at least two cameras.

8. An apparatus for detecting biomechanical and functional parameters of a knee, said apparatus comprising:

a plurality of optical markers arranged at defined anatomical points of a foot and of a corresponding knee of a person, and said defined anatomical points identify one local reference system integral with said foot and a reference point of said corresponding knee;

video recording elements calibrated with a global reference system, and configured to record at least one reference action executed in a scene by said person, and in said at least one reference action said person is executing at least one movement of support of said foot on a support plane of said scene;

baropodometric elements configured to be placed at a plantar surface of said foot in an integral way with respect to said local reference system, and configured to detect baropodometric parameters indicative of dynamic interactions exchanged between said foot and said support plan;

a processing unit configured to receive images from said video recording elements and said baropodometric parameters from said baropodometric elements;

said processing unit being provided with:

a first calculation module configured to calculate trajectories of said plurality of optical markers in said global reference system during said at least one reference action in order to identify coordinates of said defined anatomical points in said global reference system;

a second calculation module configured to calculate, from said baropodometric parameters, coordinates of a center of pressure of said foot with respect to said local reference system;

a third module of calculation configured to:

transform the coordinates of said center of pressure in said global reference system;

calculate, from said baropodometric parameters, a constraining reaction force acting on said foot;

calculate a force arm given by a distance from said center of pressure and said reference point of said corresponding knee, through the coordinates of said center of pressure and of said reference point in said global reference system;

calculate a biomechanical parameter indicative of a valgus moment and derived from a vector product of said force arm and said constraining reaction force applied on said center of pressure.

9. The apparatus of claim 8, wherein said baropodometric elements comprise at least one pressure insole capable of being inserted into a footwear worn by said foot to be subjected to said dynamic interactions.

10. The apparatus of claim 9, wherein said at least one pressure insole is provided with an array of sensors placed in a baropodometric reference system associated in an integral way with said local reference system of said foot;

the second module of calculation of said processing unit being configured to calculate the coordinates of said center of pressure in said baropodometric reference system;

the third module of calculation of said processing unit being configured to transform the coordinates of said center of pressure from said baropodometric reference system to said global reference system through said local reference system.

11. The apparatus of claim 8, wherein said video recording elements comprise at least two cameras.

* * * * *